United States Patent
Chipman et al.

(10) Patent No.: US 7,166,749 B2
(45) Date of Patent: Jan. 23, 2007

(54) PROCESS FOR PREPARING CHIRAL AROMATIC α-HYDROXY KETONES USING 2-HYDROXY-3-OXOACID SYNTHASE

(75) Inventors: David M. Chipman, Omer (IL); Ze'ev Barak, Beer-Sheva (IL); Stanislav Engel, Beer-Sheva (IL); Maria Vyazmensky, Har Hebron (IL)

(73) Assignee: Ben-Gurion University of the Negev, Beer-Sheva (IL)

( * ) Notice: Subject to any disclaimer, the term of this patent is extended or adjusted under 35 U.S.C. 154(b) by 0 days.

(21) Appl. No.: 10/502,426

(22) PCT Filed: Jan. 23, 2003

(86) PCT No.: PCT/IL03/00057

§ 371 (c)(1),
(2), (4) Date: Jan. 27, 2006

(87) PCT Pub. No.: WO03/062436

PCT Pub. Date: Jul. 31, 2003

(65) Prior Publication Data

US 2006/0148042 A1    Jul. 6, 2006

(30) Foreign Application Priority Data

Jan. 24, 2002   (IL) ..................... 147823

(51) Int. Cl.
*C07C 45/00*    (2006.01)
(52) U.S. Cl. .................. 568/314; 568/315; 568/319
(58) Field of Classification Search ................ None
See application file for complete search history.

(56) References Cited

U.S. PATENT DOCUMENTS 6,004,789 A    12/1999    Bruhn et al.

FOREIGN PATENT DOCUMENTS

| CZ | 93627 | 1/1960 |
|---|---|---|
| DE | 51651 | 2/1967 |
| DE | 195 23 269 A1 | 6/1995 |
| EP | 1048737 | 11/2000 |
| JP | 63242554 | 4/1990 |
| JP | 9-234090 | 9/1997 |
| JP | 08044976 | 9/1997 |
| JP | 2000-93189 | 4/2000 |
| WO | WO 90/04631 | 5/1990 |
| WO | WO 99/63103 | 12/1999 |
| WO | WO 01/44486 | 6/2001 |

OTHER PUBLICATIONS

Crout, et al.; *Applications of Hydrolytic and Decarboxylating Enzymes in Biotransformations*; Biocatalysis; 1994; pp. 1-30; vol. 9; Harwood Academic Publishers GmbH (XP 000671797).
Hanc O. et al., Naturwissensenschaften (1956) 43, 498.
Bruhn, et al.; *The Replacement Of Trp392 by Alanine Influences the Decarboxylase/Carboligase Activity and Stability of Pyruvate Decarboxylase from Zymomonas mobilis*, Eur. J. Biochem; 1995; pp. 650-655; vol. 234.
Barak, et al.; *Physiological Implications of the Specificity of Acetohydroxy Acid Synthase Isozymes of Enteric Bacteria*; Journal of Bacteriology; Aug. 1987; pp. 3750-3756; vol. 169, No. 8; American Society for Microbiology.
Gollop, et al.; *Kinetics and Mechanism of Acetohydroxy Acid Synthase Isozyme III from Escherichia coli*; Biochemistry; 1989; pp. 6310-6317; vol. 28, No. 15; American Chemical Society.
Ibdah, et al.; *Homology Modeling of the Structure of Bacterial Acetohydroxy Acid Synthase and Examination of the Active Site by Site-Directed Mutagenesis*; Biochemistry; 1996; pp. 16282-16291; vol. 35; No. 50; American chemical Society.
Bar-Ilan, et al.; *Binding and Activation of Thiamin Diphosphate in Acetohydroxyacid Synthase*; Biochemistry; 2001; pp. 11946-11954; vol. 40, No. 39; American Chemical Society.
Mendel, et al.; *The N-terminal Domain of the Regulatory Subunit is Sufficient for Complete Activation of Acetohydroxyacid Synthase III from Escherichia coli*; J. Mol. Biol.; 2003; pp. 275-284; vol. 325; Elsevier Science Ltd.

*Primary Examiner*—Sikarl A. Witherspoon
(74) *Attorney, Agent, or Firm*—Alston & Bird LLP

(57) ABSTRACT

A biotransformation process for preparing chiral aromatic-hydroxy ketones in high yields is described, using 2-hydroxy-3-oxoacid synthase, such as AHAS or TSAS. Optionally substituted arylaldehydes and -oxoacids react in this process to provide pure enantiomers, useful as synthons in the production of various drugs, an example being (R)-phenylacetyl carbinol.

67 Claims, No Drawings

PROCESS FOR PREPARING CHIRAL AROMATIC α-HYDROXY KETONES USING 2-HYDROXY-3-OXOACID SYNTHASE

This application is a 371 of PCT/IL03/00057, filed Jan. 23, 2003, and published as WO 03/062436, on Jul. 31, 2003.

FIELD OF THE INVENTION

The present invention relates to a biotransformation process for preparing chiral aromatic α-hydroxy ketones, including PAC, from optionally substituted arylaldehydes and 2-oxoacids using 2-hydroxy-3-oxoacid synthases, such as enzymes related to the AHAS family.

BACKGROUND OF THE INVENTION

The stereospecificity (enantiospecificity) is very important for the function of bioactive compounds, such as drugs, as only one of the enantiomers usually has the desired biological activity, while the other is inactive or even toxic. Therefore, a chemical synthesis of such molecules must involve a strenuous step of separating enantiomers at some stage of the process, or said synthesis must start with a single enantiomer of a chiral precursor (a chiral synthon). The use of enzymes in the synthesis of organic compounds, beside lowering the formation of byproducts and providing high reaction rates under mild reaction conditions, obviates the above mentioned predicaments of purely chemical synthesis, since the enzymatic reactions are regioselective and stereospecific. Many biotechnologies take advantage of biocatalysis, using either free enzymes or cells containing them.

Chiral α-hydroxyketones are versatile building blocks for the organic and pharmaceutical chemistry, e.g., for the synthesis of vitamin E, certain antifungals, antidiabetics, etc. One important chiral α-hydroxyketone is (R)-phenylacetyl carbinol ((R)-PAC), used as a synthon in the production of various drugs having α and β adrenergic properties, including L-ephedrine, pseudoephedrine, norephedrine, norpseudoephedrine, and phenylpropanolamine. These drugs are used as decongestants, antiasthmatics, vasoconstrictors, etc.

For many decades, (R)-PAC has been obtained by biotransformation of benzaldehyde using various species of fermenting yeast, mostly *Saccharomyces cerevisiae* (Scheme 1).

Scheme 1

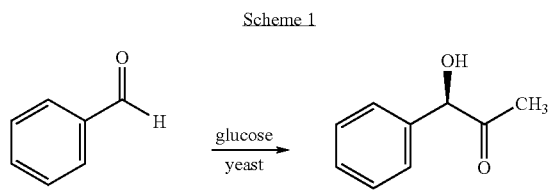

The activity of the enzyme pyruvate decarboxylase (PDC) is responsible for the formation of PAC in the yeast [Hanc O. et al., Naturwissenschaften 43 (1956) 498], in a synthetic side reaction accompanying the enzyme's normal decarboxylation of pyruvate to acetaldehyde.

Like other biotransformations using cells, the above process is limited by toxicity of benzaldehyde towards the yeast cells, and by formation of many by-products, for example benzyl alcohol, due to the action of different cellular enzymes. These factors reduce the yield of the target product, and complicate the purification procedure. Czech patent CS 93627 (1960) describes pretreating the yeast cells by strong acids to increase their resistance toward the reaction mixture before starting the biotransformation of molasses, crude sucrose, and benzaldehyde to PAC. East German patent DD 51651 (1966) describes dosing acetaldehyde together with benzaldehyde to a yeast fermentation broth to push the reaction to the direction of required products. WO 9004631 (1990) uses yeasts *Saccharomyces cerevisiae* or *Candida flarei* improved by mutagenesis in a biotransformation of benzaldehyde and pyruvate to PAC. The Japanese publication JP 09234090 (1997) describes the manufacture of (1R,2S)-1-phenyl-1,2-propanediol by a biotransformation of benzaldehyde and pyruvate using *Saccharomyces cerevisiae*. WO 9963103 (1999) relates to a biotransformation of a substituted aromatic aldehydes and pyruvate to the corresponding hydroxyl ketones, comprising yeast-mediated catalysis in organic solvents. Publication JP 2000093189 (2000) describes manufacturing optically active α-hydroxyketones using yeasts from the genera *Torulopsis* and *Candida*. In publication WO 0144486 (2001), substituted or unsubstituted aromatic aldehydes and pyruvate condense to produce carbinol compounds using yeast, in the presence of a supercritical liquid or a liquefied gas.

Application of pure enzymes as catalysts of the desired reaction has a potential to overcome some drawbacks of the whole-cell biotransformation. The synthetic potential of pyruvate decarboxylases (PDC) from *S. cerevisiae* and *Zymomonas mobilis* and benzoylformate decarboxylase from *Pseudomonas putida* has been investigated [E.g., Crout D. H. G. et al., Biocatalysis 9 (1994) 1–30]. When developing a reliable industrial process based on the purified enzymes for producing (R)-PAC, two factors are of primary importance—the efficiency of (R)-PAC formation and the stability of the enzyme under production conditions. Bruhn et al. [Eur. J. Biochem 234 (1995) 650–6; and DE 19523269 (1996)] improved the catalytic properties of PDC of *Zymomonas mobilis* by means of site-directed mutagenesis. However, the overall efficiency of the pyruvate utilization for the carboligation reaction remained very low, with only 3.5% of the pyruvate being converted to the desired product, and the bulk of pyruvate undergoing decarboxylation to acetaldehyde.

It is therefore an object of this invention to provide a biotransformation process for the preparation of chiral aromatic α-hydroxy ketones, including PAC, in a high yield from optionally substituted arylaldehydes and α-keto-acids. We have carried out systematic studies of acetohydroxyacid synthases (AHAS; belonging to the international classification group EC 4.1.3.18; known also as acetolactate synthase). The normal physiological reaction catalyzed by AHAS is decarboxylation-condensation of two α-keto acids (Scheme 2), producing an (S)-acetohydroxy acid, and requiring no additional driving force or redox agents. No regeneration of cofactors such as ATP or NAD are needed for the synthesis, only flavine adenine dinucleotide cofactor (FAD), thiamin pyrophosphate (TPP), and a divalent metal ion must be present.

Scheme 2

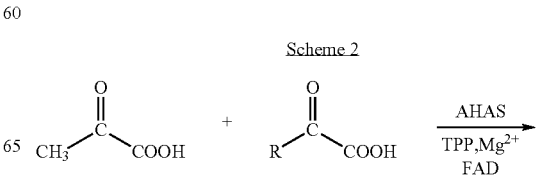

-continued

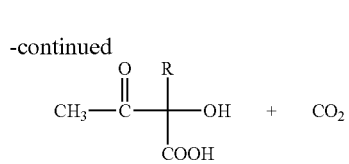

We have discovered that AHAS enzymes can also utilize "unnatural" substrates [Barak Z. et al., J. Bacteriol. 169 (1987) 3750–6; Gollop N. et al., Biochemistry 28 (1989) 6310–7; and Ibdah M. et al., Biochemistry 35 (1996) 16282–91].

Another 2-hydroxy-3-oxoacid synthase, tartronate semialdehyde synthase (TSAS; belonging to the international classification group EC 4.1.1.47; known also as glyoxylate carboligase) is closely related to AHAS, not only by its catalytic activity, but also by its sequence, as well as by other properties. Its normal physiological reaction is also decarboxylation-condensation of two 2-oxoacids, and it usually produces tartronic acid semialdehyde from glyoxylic acid (Scheme 3).

Scheme 3

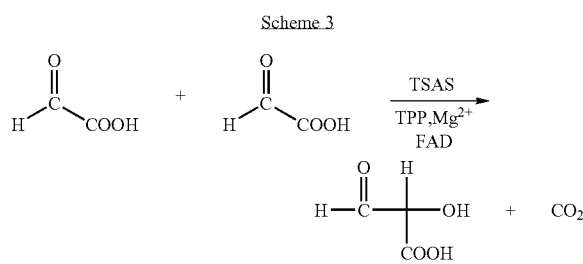

We have found that TSAS can also utilize unnatural substrates as its reactants.

It is therefore a further object of this invention to provide a biotransformation process for preparing chiral aromatic α-hydroxy ketones, including PAC, from optionally substituted arylaldehydes and 2-oxoacids using a 2-hydroxy-3-oxoacid synthase related to the AHAS family.

SUMMARY OF THE INVENTION

The present invention relates to a biotransformation process for preparing aromatic chiral α-hydroxy ketones, including PAC, from optionally substituted arylaldehydes and 2-oxoacids in high yields using a 2-hydroxy-3-oxoacid synthase, such as AHAS or tartronate semialdehyde synthase. Said biotransformation process comprises preparing a compound of formula (I)

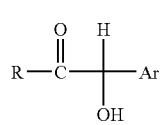

(I)

wherein R is H or $C_{1-6}$ alkyl and Ar is aryl, wherein said aryl is an aromatic system optionally containing one or more heteroatoms chosen from N, S, and O, and optionally consisting of fused rings and said alkyl and aryl are optionally substituted by 1 to 3 substituents chosen from $C_{1-3}$ alkyl, $C_{1-3}$ alkoxy, F, Cl, Br, I, OH, $NH_2$, CN, and $NR_1R_2$, wherein $R_1$ and $R_2$ can be independently H or $C_{1-4}$ alkyl, and said $C_{1-3}$ alkyl can be further substituted by a substituent chosen from F, Cl, Br, I, and OH, by reacting a compound of formula (II)

(II)

with a compound of formula (III)

(III)

wherein Ar and R in formulae (II) and (III) have the meaning defined above, in the presence of a mixture comprising the 2-hydroxy-3-oxoacid synthase, a buffer, TPP, FAD, and magnesium ions, or other divalent metal cations being able to replace magnesium in activating the enzyme.

The biotransformation process according to this invention exhibits high carboligation efficiency, since less than 1% of the compound of formula (III) is lost in decarboxylation to RCH=O. Further, by appropriate choice of conditions, either more than 98% of the compound of formula M or more than 99% of the compound of formula II, can be converted to the desired product I.

Another feature of the process according to this invention is chirality of the product which is a chiral aromatic α-hydroxy ketone, such as (R)-arylacyl carbinol. In one aspect of the invention, the substrates are pyruvate and benzaldehyde, and the product is PAC, with enantiomeric excess of (R)-PAC exceeding 97%.

The process of this invention relates to an enzymatic reaction, taking advantage of special properties of 2-hydroxy-3-oxoacid synthases related to the AHAS family, such as acetolactate synthase and tartronate semialdehyde synthase. The process can use plant or bacterial AHAS or TSAS enzymes, which can be wild types, recombinant, engineered, and mutated, and they can be immobilized or otherwise stabilized.

DETAILED DESCRIPTION OF THE INVENTION

It has now been found by us that AHAS and TSAS enzymes can efficiently catalyze the condensation reaction of aromatic aldehydes and 2-oxoacids to form chiral α-hydroxyketones. We have examined the stereospecificity of the reaction, and have found that (R)-arylacylcarbinols are formed in high enantiomeric excess when substituted benzaldehydes react with 2-oxoacids.

The biotransformations were performed in a mixture containing a buffer, $Mg^{2+}$, TPP, FAD, two substrates, and an AHAS or TSAS enzyme. The overall balance can be depicted as shown in scheme 4, wherein R and Ar have the same meaning as defined in the Summary of the Invention.

Scheme 4

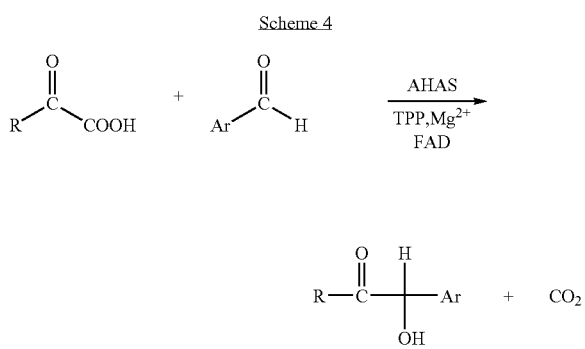

The mixture was extracted with ethyl ether or other organic solvent at the end of the enzymatic reaction, and the products were analyzed with GC equipped with FID and MS detectors. The structures of the products were confirmed by $^1$H-NMR spectroscopy and by the measurement of optical rotation. The enantiomeric purity of the products was determined by GC with an FID detector, using a column with a chiral stationary phase. The rate of consumption of aldehyde derivatives was also followed by spectrophotometry.

The reaction mixture in which a biotransformation process according to the invention is performed contains a buffer keeping pH preferably from 6 to 9, its concentration being between 0.01 M and 0.25 M, and which is preferably chosen from the group consisting of, but not being limited by, MES, BIS-TRIS, PIPES, BES, MOPS, TES, HEPES, TRIS, Tricine, Bicine, and phosphate. The reaction mixture further contains TPP, FAD, magnesium ions, two substrates in concentrations between 0.1 mM and 100 mM, and optionally one or more non-buffering salts in the total concentration from 0 to 150 mM. Magnesium ions can optionally be replaced by other divalent metal cations being able to activate the enzyme, such as calcium, barium, manganese, zinc, cobalt, and nickel. The mixture optionally contains a water-miscible organic solvent, preferably chosen from the group consisting of, but not being limited by, 2-propanol, dimethyl sulfoxide, dimethyl formamide, and acetamide, in concentrations from 0 to 50% (v/v). The concentration of enzyme is either 0.01–1.0 mg/ml or 0.1–10 U/ml, wherein the units represent μmol of α-hydroxy ketone formed/min. The reaction mixture optionally contains a reducing agent, such as dithiothreitol (DTT), in concentrations between 0.01 and 10 mM to improve enzyme stability. The preferred temperature of the mixture is between 15 and 40° C.

In a preferred embodiment, the biotransformation process according to the invention comprises pH 6.5–7.5, temperature 30° C., mild stirring, 1 mM $Mg^{2+}$, 0.1 mM TPP, 0.05 mM FAD, and 60 mM KCl.

It was found that the by-product formation in the reaction catalyzed by AHAS was dependent on the substrate concentrations. Further, it was found that the arylaldehyde was not consumed in any oxidative side-reaction, as indicated by an insignificant effect of the oxygen concentration on the aldehyde consumption and absence of oxidation products detected by HPLC.

In a preferred embodiment of a biotransformation according to this invention, the 2-hydroxy-3-oxoacid synthase enzyme is the wild type AHAS isozyme II from *Escherichia coli* (WT) prepared as described in Bar-Ilan et al. [Biochemistry 40 (2001) 11946–54]. In another preferred embodiment of this invention, the AHAS enzyme is a recombinant AHAS isozyme II with an N-terminal fusion allowing affinity purification. In another preferred embodiment of this invention, the AHAS enzyme is a recombinant AHAS isozyme I with an N-terminal fusion. According to other embodiments of this invention, AHAS comprises an enzyme chosen from bacterial enzyme, yeast enzyme, fungal enzyme, and plant enzyme.

In a preferred embodiment of this invention, pyruvate reacts with optionally substituted benzaldehyde in the presence of AHAS isozyme II. We measured the concentrations of two expected compounds derived from the enzymatic condensation of pyruvate with benzaldehyde during said reaction, namely PAC and 2-hydroxypropiophenone (2-HPP) (Scheme 5) by GC and HPLC.

Scheme 5

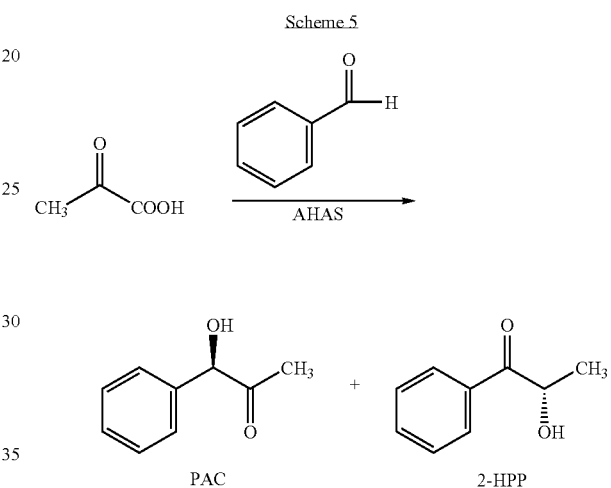

The products 2-HPP constituted less than 0.2–0.8% of the total product when the reaction was worked up without heating. The oxidation product phenylpropanedione (PPD) cannot be detected under the preferred conditions of storage, constituting less than 0.1% of the product. PPD is only detected after prolonged storage. The absolute configuration of PAC was found to be R(−).

The specific activity of the AHAS enzyme used in the above biotransformation, based on the initial velocity of PAC formation, was found to be higher than 3 U/mg. In a biotransformation using recombinant AHAS I, the efficiency of the carboligation in the condensation of benzaldehyde and pyruvate was more than 98% based on pyruvate consumed when benzaldehyde was present in excess, and more that 99% based on benzaldehyde when pyruvate was in excess. The enantiomeric excess of the (R)-PAC formed in the reaction was found to be ≧97%.

Some advantages of the present invention can be seen from a comparison with the prior art. The following table compares biotransformations performed according to this invention and according to U.S. Pat. No. 6,004,789 which used a mutant pyruvate decarboxylase from *Zymomonas mobilis*.

The table shows that WT AHAS II exhibits better parameters in the biotransformation than a PDC enzyme, even if said PDC enzyme was used only after improving its active site by a mutation, while the AHAS enzyme was used here directly as a wild type. The active site of the AHAS enzymes seems to be better designed to accommodate the second substrate for the condensation reaction than the active site of PDC enzymes.

TABLE 1

(R)-PAC synthesis by a mutant Z.m. PDC (U.S. Pat. No. 6,004,789) and WT AHAS II

|  | Mutant Z.m. PDC | WT AHAS II |
| --- | --- | --- |
| Efficiency of carboligation based on pyruvate | 3.5% | >98% (with excess benzaldehyde) |
| Specific activity | >1 U/mg | >3 U/mg |
| 2-HPP formation | cca. 5% | <1% |
| Enantiomeric excess | cca. 95% | ≧97% |

In another embodiment of the present invention, a mutated WT AHAS II enzyme is used, wherein the mutation changes the specificity of the enzyme, or increases its specific activity. In one of preferred embodiments, enzyme W464L is used, which is an engineered, recombinant hexahistidine-tagged fusion protein based on WT AHAS II, overexpressed in E. coli, having a single mutation. The mutation W464L, known to decrease the specificity of the enzyme for 2-ketobutyrate over pyruvate as second substrate in the natural reaction [Ibdah M. et al., Biochemistry 35 (1996) 16282–91], decreases the sensitivity of the enzyme to inhibition by high concentrations of the substrate benzaldehyde or by the product PAC, compared to the wild protein. In another preferred embodiment, enzyme M250A is used, which is another engineered, recombinant fusion protein based on WT AHAS II having a single mutation. Mutant M250A exhibits the same rate of (R)-PAC formation as the wild-type enzyme, but it shows a lower rate of formation of the normal AHAS product acetolactate (AL), resulting in the improved efficiency of (R)-PAC formation. These findings show possibilities for other modifications of the enzyme that could change the properties of the enzyme in the desired direction, including increasing the specificity toward certain substrates, or increasing the activity, or improving stability and resistance to inactivation by substrates and products.

In another preferred embodiment, a recombinant hexahistidine-tagged fusion protein based on WT AHAS I, overexpressed in E. coli, is used. This enzyme is able to convert acetolactate to (R)-PAC in the presence of benzaldehyde, so that the yield of (R)-PAC is maximized, despite the fact that the initial rate of formation of acetolactate is higher than the rate of formation of PAC, when pyruvate and benzaldehyde are present in equimolar amounts.

In other preferred embodiments of this invention, a oxoacid chosen from glyoxylic acid, pyruvic acid, 2-ketobutyric acid, and 2-ketovaleric acid, reacts with an aryl aldehyde, wherein aryl is chosen from phenyl, naphthyl, benzyl, pyridinyl, furyl, and thienyl.

In another preferred embodiment of this invention, an optionally substituted benzaldehyde reacts with pyruvate in the presence of AHAS isozyme I. In the condensation of pyruvate with 3-hydroxybenzaldehyde catalyzed by WT AHAS I, we found that >99% of the 3-hydroxybenzaldehyde was consumed. Similarly, conversions to hydroxyketones of >90% were found with AHAS isozyme I, when reacting pyruvate with an aldehyde chosen from 4-hydroxybenzaldehyde, 3-methoxy-, 4-methoxybenzaldehyde, 2-methyl-, 3-methyl and 4-methylbenzaldehyde, 3-cyano- and 4-cyanobenzaldehyde, 2-formylpyridine, 3-formylpyridine, 4-formylpyridine, 2-formylnaphthalene, and chlorobenzaldehyde.

The present invention thus provides a process for the synthesis of certain chiral α-hydroxy ketones, including precursors of the drugs related to ephedrine, using a 2-hydroxy-3-oxoacid synthase related to the AHAS family. The enzyme can be in various forms, as is known to those skilled in the art, including a crude protein or a pure enzyme, comprising either a free non-stabilized enzyme or a stabilized enzyme, eventually immobilized. The components of the enzymatic reaction can be added to the reaction mixture in one portion, or they can be added continually. The reaction can be carried out in a two-phase system with an immiscible or partially miscible non-aqueous solvent. The products of the biotransformation process according to this invention can be isolated according to methods known in the art, for example by extracting from the water phase to diethyl ether, followed by further purification according to known methods.

As has been said, this invention relates to a biotransformation process of preparing an aromatic α-hydroxy ketone of formula (I)

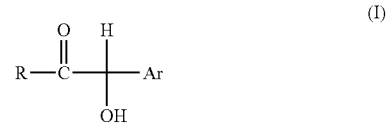

wherein R is H or $C_{1-6}$ alkyl, and Ar is aryl, wherein said aryl is an aromatic system optionally containing one or more heteroatoms chosen from N, S, and O, and optionally consisting of fused rings, and said alkyl and aryl are optionally substituted by 1 to 3 substituents chosen from $C_{1-3}$ alkyl, $C_{1-3}$ alkoxy, F, Cl, Br, I, OH, $NH_2$, CN, and $NR_1R_2$, wherein $R_1$ and $R_2$ can be independently H or $C_{1-4}$ alkyl, and said $C_{1-3}$ alkyl can be further substituted by a substituent chosen from F, Cl, Br, I, and OH, by reacting an aldehyde of formula (II)

with a 2-oxoacid of formula (III)

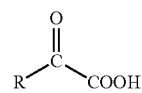

wherein Ar and R in formulae (II) and (III) have the meaning defined for formula (I), in the presence of a mixture comprising a 2-hydroxy-3-oxoacid synthase chosen from AHAS and tartronic semialdehyde synthase, a buffer, TPP, FAD, and magnesium or other divalent metal cation being able to activate the enzyme.

EXAMPLES

Materials and Procedures

Materials

Sodium pyruvate, FAD, TPP, benzaldehyde, and other aromatic aldehydes were obtained from Sigma-Aldrich. All other materials were of analytical grade.

Biocatalyst

AHAS isozyme II from *Escherichia coli*, wild type (WT) was obtained as a N-terminal hexahistidine-tagged protein overexpressed in *E. coli* BL21/pRSETilvGM strain, as were mutants AHAS II W464L and AHAS II M250A. The genes ilvBN encoding AHAS I were amplified together by PCR from DNA of *E. coli* and inserted into expression vector pET28(c). The resulting plasmid, expressing a hexahistidine-tagged fusion protein of AHAS I, was transformed into *E. coli* BL21. Bacterial growth and cloned gene expression were carried out as described elsewhere [Bar-Ilan et al., Biochemistry 40 (2001) 11946–54]. Proteins were purified on a Ni-NTA Agarose column (Qiagen, Hilden, Germany), with the non-denaturing protocol previously described [Mendel et al., J Mol Biol 325 (2003) 275–84].

Enzymatic Reaction Rate

The reaction could be followed by one of several methods. In a direct spectroscopic assay for consumption of the aromatic aldehyde, the initial rate of the enzymatic reaction was determined by the rate of benzaldehyde disappearance followed spectroscopically at wavelength of 302 nm ($\epsilon$=454 $M^{-1}cm^{-1}$). Enzymatic reaction was carried out at 37° C. in a 1 ml quartz cuvette in a Beckman spectrophotometer (DU 640) in an appropriate buffer containing sodium pyruvate and benzaldehyde or substituted benzaldehyde. Reaction was initiated by addition of AHAS II to a final concentration of 0.2–0.5 mg/ml. As much as 2% of a water miscible organic solvent such as isopropanol, dimethylsulfoxide, etc., can be added to aid in dissolution of the benzaldehyde.

The possibility that benzaldehyde is consumed in an oxidative side-reaction was tested by running the reaction under low oxygen tension (bubbling $N_2$ through the reaction solution); no significant effect of oxygen on the rate of benzaldehyde consumption was observed.

The initial rate of formation of PAC and acetolactate in an enzymatic reaction could also be determined simultaneously by a differential creatine-naphtol calorimetric method related to the Westerfeld assay with some modifications. Reaction was initiated by the addition of AHAS to a reaction mixture containing buffer, substrates, and cofactors. At different times, 500 µl aliquots of the reaction mixture were taken and added to 50 µl of 50% (v/v) $H_2SO_4$ to terminate the reaction. The samples were incubated 15 min at 37° C. to bring about the conversion of acetolactate to acetoin. Portions of the quenched sample (5–150 µl) were brought to 1.4 ml, and 1 ml of 0.5% creatine solution, and 1 ml of 5% solution of naphtol (in 2.5 N NaOH) were added. After 15 min incubation at 37° C. the absorbance was determined at wavelengths of 490 and 580 nm on a Beckman spectrophotometer. The colored products derived from PAC and acetolactate have different absorbance spectra, allowing the simultaneous determination of the concentration of both products.

The progress of the reaction to form PAC and its isomer 2-HPP was alternatively followed by HPLC on a $C_{18}$-TSKgel column (250 mm×4.6 mm) with 30% acetonitrile/ 0.5% acetic acid (v/v) as eluent, using a Waters 600 E solvent delivery system and Jasco MD-2010 diode array spectrometer. This did not allow detection of acetolactate.

Biotransformation

Reaction was performed in a mixture containing 0.1 M PIPES-KOH, pH 6.5, 1 mM $MgCl_2$, 60 mM KCl, 0.1 mM TPP, and 0.05 mM FAD, in the presence of 5–30 mM sodium pyruvate and benzaldehyde at a 1:1 ratio. Isopropanol (2% final) was used to aid in dissolution of benzaldehyde. AHAS isozyme II was added to the final concentration of 0.3 mg/ml to start the reaction. At the end of the enzymatic reaction, mixture was extracted twice with 10 ml of ethyl ether. The organic phase was dried with $MgSO_4$, the solvent was removed in vacuo, and the products were separated and analyzed by GC-MS.

Analysis After Biotransformation

The products were analyzed with GC system equipped with MS detector (Hewlett Packard). Separation was performed on a RTX-1 30 m capillary column using helium as carrier gas. The injector temperature was 250° C. The column temperature regimen was: 5 min at 50° C., and then increase to 250° C. at 15° C./min. The retention times were: 11.9 min for PPD, 12.7 min for PAC, and 13.1 min for 2-HPP. A flame ionization detector (220° C.) was used to evaluate relative amounts of the compounds. The identification of products was confirmed by $^1$H-NMR spectroscopy.

The enantiomeric purity of PAC was determined by GC using Lipodex E 0.25 µm chiral column (0.25 mm×25 m) with hydrogen as carrier gas. The operating conditions were: 200° C. an injector, 120° C. a column, and 220° C. a FID detector. The retention times were: 10.23 min for (S)-PAC and 11.34 min for (R)-PAC. Optical rotation was measured in chloroform using a Perkin-Elmer 341 polarimeter.

Example 1

A 1 ml quartz cuvette containing 1 ml of the reaction mixture containing 5 mM of sodium pyruvate and 5 mM of benzaldehyde, in a reaction buffer contained 0.1 M Tricine-HCl, pH 7.5, 1 mM $MgCl_2$, 60 mM KCl, 0.1 mM TPP, and 0.05 mM FAD, was placed in the spectrophotometer at 37° C. Reaction was started by addition of 10 µl of an AHAS isozyme II solution containing 33 mg enzyme/ml. The absorbance value at 302 nm decreased linearly at a rate of 0.161 OD/min, which yielded a decrease of benzaldehyde concentration of 0.36 µmol/min, when using $\epsilon$=454 $M^{-1}cm^{-1}$. The corresponding activity was 1.07 U/mg.

Example 2

The reaction rate was measured as described in Example 1, using as substrates 5 mM pyruvate and 5 mM 3-hydroxybenzaldehyde. The absorbance values at 346 nm decreased linearly at a rate of 0.15 OD/min, which yielded a decrease of hydroxybenzaldehyde concentration 0.3 µmol/min, when using $\epsilon$=480 $M^{-1}cm^{-1}$. The corresponding activity was 0.93 U/mg.

Example 3

Two 20 ml flasks, each containing ten ml of the reaction mixture as described above in the paragraph Biotransformation, were shaken at 30° C. One of the flasks contained substrates at the concentrations of 10 mM, the other one of 30 mM. The reaction started by addition of 3 mg of AHAS isozyme II, and was ended after 1 h by adding 10 ml diethyl ether, and extracting, followed by second extraction with 10 ml. The extract was dried as described, evaporated to completely remove solvent and redissolved in dichloromethane. This sample was analyzed by GC-MS and GLC using FID detection. Mass spectrum showed three components corresponding to phenylacetyl carbinol (PAC), 2-hydroxypropiophenone (2-HPP), and phenylpropanedione (PPD). The following table shows the relative areas corresponding to the three products by FID.

TABLE 2

| | GLC, FID detector, % areas. | | |
|---|---|---|---|
| Substrates | PAC | 2-HPP | PPD |
| 10 mM | 80 | 15 | 5 |
| 30 mM | >99 | not detectable | not detectable |

Example 4

A flask, containing 50 ml of 40 mM benzaldehyde and 70 mM pyruvate (2 mmol and 3.5 mmol total, respectively) in 0.1 M HEPES/KOH, pH 7.0, 5 mM $MgCl_2$, 0.1 mM TPP, 0.05 mM FAD, 60 mM KCl, 0.5 mM DTT, was slowly stirred at 30° C. The reaction was started by addition of 16 mg of AHAS isozyme I, and was ended after 1.5 h by adding 50 ml diethyl ether, and extracting, followed by second extraction with 50 ml. The extract was dried over $MgSO_4$, evaporated to completely remove solvent and a sample was redissolved in chloroform. This sample was analyzed by GC-MS and GLC using FID detection. Mass spectrum showed three components corresponding to phenylacetyl carbinol (PAC), 2-hydroxypropiophenone (2-HPP), and phenylpropanedione (PPD). The following table shows the relative areas corresponding to the three products detected by FID.

TABLE 3

| Area percent of FID/GC peaks | | |
|---|---|---|
| PAC | 2-HPP | PPD |
| 99.1 | 0.7 | 0.2 |

The conversion of benzaldehyde to products was >99% by HPLC and GC. After workup, 264 mg of PAC with final purity of 98.6% (1.74 mmol of pure PAC) was obtained comprising 87% of the theoretical yield (2 mmol PAC). The sample was analyzed by GC using a chiral column and FID, and optical activity was checked by polarimeter. The optical rotation was negative (left), confirming that the product was (−)-(R)-PAC. The enantiomeric excess of this (R)-PAC was >97%.

Example 5

One ml of the reaction mixture containing 30 mM 3-hydroxybenzaldehyde and 50 mM sodium pyruvate, in a buffer described in the above example, was gently agitated at room temperature. The reaction was started by addition of 0.5 mg of AHAS isozyme I, and was ended after 1 h by adding 1 ml chloroform, and extracting, followed by high speed centrifugation. The organic phase samples were analyzed by GC-MS and GC using FID detection. The analysis showed a complete conversion of 3-hydroxybenzaldehyde to the products. Mass spectrum showed three components corresponding to 3-hydroxy-phenylacetylcarbinol (3-OH-PAC), 1-(3-hydroxyphenyl)-2-hydroxypropan-1-one (HPH), and 1-(3-hydroxyphenyl)-propane-1,2-dione (HPP). The following table shows the relative areas corresponding to the three products detected by FID.

TABLE 4

| Area percent of FID/GC peaks, | | |
|---|---|---|
| 3-OH-PAC | HPH | HPP |
| 95.6 | 3.2 | 1.2 |

Example 6

The enzymatic reaction rate was measured as described in Example 1, using the mutants of AHAS II: W464L and M250A, each comprising a single site-directed mutation. The activities 1.72 and 1.66 U/mg (1 U=1 µmol benzaldehyde consumed/min) respectively, were found. This showed that substitution of the amino acids involved in the formation of a binding pocket for a second substrate (according to the structural model), may lead to the improvement of the catalytic properties of the enzyme.

Example 7

A mixture containing 30 mM benzaldehyde and 30 mM pyruvate in 0.1 M HEPES/KOH, pH 7.0, 5 mM MgCl2, 0.1 mM TPP, 0.05 mM FAD, 60 mM KCl, 0.5 mM DTT, was incubated at 30° C. The reaction was started by addition of 0.32 mg/ml of AHAS II mutant M250A, comprising a single site-directed mutation. Initial rates of PAC and AL formation were measured by the differential colorimetric method, and were found to be 2.7 and 0.24 µmol $min^{-1}mg^{-1}$ respectively. The calculated final concentrations of PAC and AL after 2 h of the reaction were 18 mM and 2 mM, respectively. This showed that substitution of the amino acids involved in the substrate binding pocket or access channel, may lead to the improved yields in the enzymatic process by increasing specificity for benzaldehyde and decreasing by-product formation.

While this invention has been described in terms of some specific examples, many modifications and variations are possible. It is therefore understood that within the scope of the appended claims, the invention may be realized otherwise than as specifically described. It was shown that enzymes related to the AHAS family, such as acetolactate synthases and tartronate semialdehyde synthases, can accept different aldehydes as substrates, and it was also shown that a mutation of a wild enzyme can change the properties of the enzyme in a desired direction. A skilled person will appreciate that other enzymes related to EC 4.1.3.18 or EC 4.1.1.47 can be used for realizing the present invention. The newly discovered properties of said enzymes have a great potential for competing with existing biocatalytic processes, for producing a variety of chiral α-hydroxy ketones, as well as for providing new routes to other important chiral synthons.

What is claimed is:

1. A process of preparing an aromatic α-hydroxy ketone of formula (I)

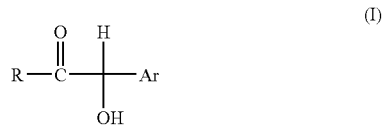

wherein R is H or $C_{1-6}$ alkyl, and Ar is aryl, wherein said aryl optionally contains one or more heteroatoms chosen from N, S and O, and optionally consists of fused rings, and said alkyl and aryl are optionally substituted by 1 to 3 substituents chosen from $C_{1-3}$ alkyl, $C_{1-3}$ alkoxy, F, Cl, Br, I, OH, $NH_2$, CN, and $NR_1R_2$, wherein $R_1$ and $R_2$ can be independently H or $C_{1-4}$ alkyl, and said $C_{1-3}$ alkyl can be further substituted by a substituent chosen from F, Cl, Br, I, and OH; which process comprises reacting an aldehyde of formula (II)

with a 2-oxoacid of formula (III)

wherein Ar and R in formulae (II) and (III) have the meaning defined for formula (I); in the presence of a mixture comprising 2-hydroxy-3-oxoacid synthase chosen from AHAS and TSAS,
and thiamin pyrophosphate (TPP), flavine adenine dinucleotide (FAD), metal ions, and a buffer.

2. A process according to claim 1, wherein one of the enantiomers of the compound of formula (I) is formed in excess.

3. A process according to claim 1, wherein the aromatic α-hydroxy ketone is chiral aromatic α-hydroxy ketone.

4. A process according to claim 1, wherein the compound of formula (I) is (R)-arylacyl carbinol.

5. A process according to claim 1, wherein the 2-oxoacid is pyruvic acid.

6. A process according to claim 1, wherein the 2-oxoacid is chosen from glyoxylic acid, 2-ketobutyric acid, and 2-ketovaleric acid.

7. A process according to claim 1, wherein the aryl is chosen from phenyl, benzyl, naphthyl, furyl, pyridinyl and thienyl.

8. A process according to claim 1, wherein the aldehyde is a substituted benzaldehyde.

9. A process according to claim 1, wherein the aldehyde is benzaldehyde.

10. A process according to claim 1, wherein the compound of formula (I) is phenylacetyl carbinol (PAC).

11. A process according to claim 1, wherein the compound of formula (I) is (R)-PAC.

12. A process according to claim 10, wherein PAC constitutes more than 95% of the products of the enzymatic reaction.

13. A process according to claim 10, wherein PAC constitutes more than 99% of the products of the enzymatic reaction.

14. A process according to claim 11, wherein (R)-PAC constitutes more than 90% of PAC produced in the enzymatic reaction.

15. A process according to claim 11, wherein (R)-PAC constitutes more than 95% of PAC produced in the enzymatic reaction.

16. A process according to claim 1, wherein said 2-hydroxy-3-oxoacid synthase comprises an enzyme of bacterial origin.

17. A process according to claim 1, wherein said 2-hydroxy-3-oxoacid synthase comprises an enzyme chosen from yeast enzyme, fungal enzyme, and plant enzyme.

18. A process according to claim 1, wherein said 2-hydroxy-3-oxoacid synthase comprises a wild type protein.

19. A process according to claim 1, wherein said 2-hydroxy-3-oxoacid synthase comprises a recombinant protein.

20. A process according to claim 1, wherein said 2-hydroxy-3-oxoacid synthase comprises an engineered protein.

21. A process according to claim 1, wherein said 2-hydroxy-3-oxoacid synthase comprises a mutant protein.

22. A process according to claim 1, wherein said 2-hydroxy-3-oxoacid synthase comprises an AHAS enzyme.

23. A process according to claim 1 wherein said 2-hydroxy-3-oxoacid synthase comprises an TSAS enzyme.

24. A process according to claim 1 wherein said 2-hydroxy-3-oxoacid synthase comprises AHAS isozyme I protein from *Escherichia coli*.

25. A process according to claim 1, wherein said 2-hydroxy-3-oxoacid synthase comprises AHAS isozyme II protein from *Escherichia coli*.

26. A process according to claim 1, wherein said 2-hydroxy-3-oxoacid synthase comprises TSAS from *Escherichia coli*.

27. A process according to claim 1, wherein said 2-hydroxy-3-oxoacid synthase comprises a histidine-tagged protein.

28. A process according to claim 1, wherein said 2-hydroxy-3-oxoacid synthase comprises specific directed mutants of AHAS II overexpressed in host cells.

29. A process according to claim 1, wherein said 2-hydroxy-3-oxoacid synthase comprises a stabilized enzyme.

30. A process according to claim 1, wherein said 2-hydroxy-3-oxoacid synthase comprises an immobilized enzyme.

31. A biotransformation process according to claim 1, wherein all the components of the enzymatic reaction are added to the reaction mixture in one portion.

32. A biotransformation process according to claim 1, wherein some of the components of the enzymatic reaction are added to the reaction mixture in more portions or continually.

33. A process according to claim 28, wherein pH of the mixture is from 5 to 9.

34. A process according to claim 28, wherein pH of the mixture is from 6.5 to 7.5.

35. A process according to claim 28, wherein the mixture comprises a buffer chosen from the group consisting of MES, BIS-TRIS, PIPES, BES, MOPS, TES, HEPES, TRIS, Tricine, Bicine, and phosphate.

36. A process according to claim 28, wherein the buffer has a concentration between 0.01 M and 0.25 M.

37. A process according to claim 28, wherein the aldehyde and the oxoacid are added to concentrations between 2 mM and 100 mM.

38. A process according to claim 28, wherein TPP and FAD are added to concentrations between 0.02 mM and 0.2 mM.

39. A process according to claim 28, wherein magnesium ions are added to a concentration between 0.2 mM and 2 mM.

40. A process according to claim 28, wherein DTT is added to a concentration between 0.1 mM and 2 mM.

41. A process according to claim 28, wherein the enzyme is added to a concentration between 0.01 mg/ml and 1.0 mg/ml.

42. A process according to claim 28, wherein the enzyme is added to a concentration between 0.1 and 10 U/ml.

43. A process according to claim 28, wherein the temperature of the mixture is between 15 and 40° C.

44. A process according to claim 1, wherein said mixture comprises a water-miscible organic solvent chosen from 2-propanol, dimethyl sulfoxide, dimethyl formamide, and acetamide, in concentrations from 0 to 50% (v/v).

45. A process according to claim 29, wherein pH of the mixture is from 5 to 9.

46. A process according to claim 29, wherein pH of the mixture is from 6.5 to 7.5.

47. A process according to claim 29, wherein the mixture comprises a buffer chosen from the group consisting of MES, BIS-TRIS, PIPES, BES, MOPS, TES, HEPES, TRIS, Tricine, Bicine, and phosphate.

48. A process according to claim 29, wherein the buffer has a concentration between 0.01 M and 0.25 M.

49. A process according to claim 29, wherein the aldehyde and the oxoacid are added to concentrations between 2 mM and 100 mM.

50. A process according to claim 29, wherein TPP and FAD are added to concentrations between 0.02 mM and 0.2 mM.

51. A process according to claim 29, wherein magnesium ions are added to a concentration between 0.2 mM and 2 mM.

52. A process according to claim 29, wherein DTT is added to a concentration between 0.1 mM and 2 mM.

53. A process according to claim 29, wherein the enzyme is added to a concentration between 0.01 mg/ml and 1.0 mg/ml.

54. A process according to claim 29, wherein the enzyme is added to a concentration between 0.1 and 10 U/ml.

55. A process according to claim 29, wherein the temperature of the mixture is between 15 and 40° C.

56. A process according to claim 1, wherein said 2-hydroxy-3- oxoacid synthase comprises specific directed mutants of AHAS I overexpressed in host cells.

57. A process according to claim 56, wherein pH of the mixture is from 5 to 9.

58. A process according to claim 56, wherein pH of the mixture is from 6.5 to 7.5.

59. A process according to claim 56, wherein the mixture comprises a buffer chosen from the group consisting of MES, BIS-TRIS, PIPES, BES, MOPS, TES, HEPES, TRIS, Tricine, Bicine, and phosphate.

60. A process according to claim 56, wherein the buffer has a concentration between 0.01 M and 0.25 M.

61. A process according to claim 56, wherein the aldehyde and the oxoacid are added to concentrations between 2 mM and 100 mM.

62. A process according to claim 56, wherein TPP and FAD are added to concentrations between 0.02 mM and 0.2 mM.

63. A process according to claim 56, wherein magnesium ions are added to a concentration between 0.2 mM and 2 mM.

64. A process according to claim 56, wherein DTT is added to a concentration between 0.1 mM and 2 mM.

65. A process according to claim 56, wherein the enzyme is added to a concentration between 0.01 mg/ml and 1.0 mg/ml.

66. A process according to claim 56, wherein the enzyme is added to a concentration between 0.1 and 10 U/ml.

67. A process according to claim 56, wherein the temperature of the mixture is between 15 and 40° C.

* * * * *